(12) United States Patent
Igarashi et al.

(10) Patent No.: US 10,336,764 B2
(45) Date of Patent: Jul. 2, 2019

(54) FULLERENE DERIVATIVE AND LUBRICANT

(71) Applicant: SHOWA DENKO K.K., Tokyo (JP)

(72) Inventors: Takeshi Igarashi, Tokyo (JP); Yasuyuki Ueda, Tokyo (JP); Kentaro Watanabe, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 15/828,987

(22) Filed: Dec. 1, 2017

(65) Prior Publication Data

US 2018/0086771 A1 Mar. 29, 2018

Related U.S. Application Data

(63) Continuation-in-part of application No. PCT/JP2016/069159, filed on Jun. 28, 2016.

(30) Foreign Application Priority Data

Jul. 3, 2015 (JP) .................................. 2015-134576

(51) Int. Cl.
| | |
|---|---|
| *C07D 487/22* | (2006.01) |
| *C07D 487/18* | (2006.01) |
| *C07D 487/08* | (2006.01) |
| *C07D 209/70* | (2006.01) |
| *C10M 105/70* | (2006.01) |
| *C10M 105/54* | (2006.01) |
| *C10M 103/02* | (2006.01) |
| *C10M 105/00* | (2006.01) |

(52) U.S. Cl.
CPC ......... *C07D 487/22* (2013.01); *C07D 209/70* (2013.01); *C07D 487/08* (2013.01); *C07D 487/18* (2013.01); *C10M 103/02* (2013.01); *C10M 105/00* (2013.01); *C10M 105/54* (2013.01); *C10M 105/70* (2013.01); *C10M 2213/0606* (2013.01); *C10M 2215/223* (2013.01); *C10N 2220/082* (2013.01); *C10N 2230/54* (2013.01); *C10N 2240/204* (2013.01); *C10N 2250/121* (2013.01); *C10N 2280/00* (2013.01)

(58) Field of Classification Search
CPC combination set(s) only.
See application file for complete search history.

(56) References Cited

U.S. PATENT DOCUMENTS

| 9,349,403 B2 | 5/2016 | Hanawa et al. |
| 2015/0162044 A1 | 6/2015 | Hanawa et al. |

FOREIGN PATENT DOCUMENTS

| EP | 3109228 | 12/2016 |
| JP | 2006-131874 | 5/2006 |

(Continued)

OTHER PUBLICATIONS

JP2006131874A Bib Translated; May 2006.*

(Continued)

*Primary Examiner* — Ellen M McAvoy
*Assistant Examiner* — Chantel L Graham
(74) *Attorney, Agent, or Firm* — IPUSA, PLLC

(57) ABSTRACT

A fullerene derivative, used as a lubricant, includes, in a molecule: a fullerene backbone; and n pyrrolidine rings each being condensed to the fullerene backbone, each of the pyrrolidine rings including one aryl group including a group including m perfluoropolyether chains, "m" being an integer from 2 to 5 and "n" being an integer from 1 to 5.

10 Claims, 2 Drawing Sheets

(56) References Cited

FOREIGN PATENT DOCUMENTS

| | | |
|---|---|---|
| JP | 2011-121886 | 6/2011 |
| JP | 2011-140480 | 7/2011 |
| JP | 2013-140923 | 7/2013 |
| JP | 2013-170137 | 9/2013 |
| JP | 2015-013844 | 1/2015 |
| JP | 2015-109129 | 6/2015 |
| JP | 2015-135710 | 7/2015 |
| WO | 2015/125940 | 8/2015 |

OTHER PUBLICATIONS

JP2006131874A Claims Translated; May 2006.*
JP2006131874A Description Translated; May 2006.*
JP2011140480A Bib Translated; Jul. 2011.*
JP2011140480A Claims Translated; Jul. 2011.*
JP2011140480A Description Translated; Jul. 2011.*
International Search Report dated Sep. 20, 2016 with respect to PCT/JP2016/069159.
Bharat Bhushan et al., "Sublimed C60 films for tribology" Appl. Phys. Lett. 62(25), Jun. 21, 1993, pp. 3253-3255.
B. M. Ginzburg et al., "Antiwear Effect of Fullerene C60 Additives to Lubricating Oils" Russian Journal of Applied Chemistry, vol. 75, No. 8, 2002, pp. 1330-1335.
Norio Shibata et al., "Trifluoroethoxy—Coating improves the Axial Ligand Substitution of Subphthalocyanine" Chemistry A European Journal, 2010, vol. 16, No. 25, pp. 7554-7562 cited in ISR for No. PCT/JP2016/069159.
Takashi Nakanishi et al., "Superstructures and superhydrophobic property in hierarchical organized architectures of fullerenes bearing long alkyl tails" Journal of Materials Chemistry, 2010, vol. 20, No. 7, pp. 1253-1260 cited in ISR for No. PCT/JP2016/069159.

* cited by examiner

FULLERENE DERIVATIVE AND LUBRICANT

CROSS-REFERENCE TO RELATED APPLICATION

This application is a continuation-in-part application filed under 35 U.S.C. 111(a) claiming the benefit under 35 U.S.C. 120 and 365(c) of PCT International Application No. PCT/JP2016/069159 filed on Jun. 28, 2016, which is based upon and claims priority to Japanese Priority Application No. 2015-134576 filed on Jul. 3, 2015, the entire contents of which are hereby incorporated by reference.

BACKGROUND OF THE INVENTION

1. Field of the Invention

The present invention relates to a fullerene derivative including perfluoropolyether (PFPE) chains and a lubricant including the fullerene derivative.

2. Description of the Related Art

As perfluoropolyether chemical compounds have large viscosity index in addition to having good heat resistance, chemical resistance and oxidation resistance, variation in fluidity (viscosity) is small over a wide temperature range from low temperature to high temperature, and show good lubricity. Further, perfluoropolyether chemical compounds have properties such as fireproof, not influencing on a high-molecular material such as rubber or plastic, low vapor pressure and low evaporation loss, low surface tension and high electric insulation, and are known to show high performance over an extremely wide range as lubricants. Thus, perfluoropolyether chemical compounds are widely used as lubricating oils for various purposes such as a vacuum pump oil, lubrication for a magnetic disk/tape or the like, a heating medium or an incoherent agent.

Meanwhile, $C_{60}$, which is a fullerene, is known to be useful as a lubricant. In Non-Patent Document 1 (Bhushan et al.: Appl. Phys. Lett. 62, 3253 (1993)), it is confirmed that a coefficient of friction is lowered in a silicon substrate on which a deposited film of $C_{60}$ is formed. Although Non-Patent Document 1 suggests a fullerene derivative in which a perfluoropolyether group is introduced in a fullerene, a specific chemical compound or a method of manufacturing it are not described.

Further, $C_{60}$ is known to show good properties as an additive for a conventional lubricating oil. In Non-Patent Document 2 (Ginzburget et al.: Russian Journal of Applied Chemistry 75, 1330 (2002)), it is confirmed that abrasion resistance is improved by adding $C_{60}$ to a lubricating oil, compared with a case when $C_{60}$ is not added.

Patent Document 1 (Japanese Laid-open Patent Publication No. 2006-131874) discloses a lubricant composed of a mixture of $C_{60}$, a $C_{60}$ derivative including a carboxyl group, a hydroxylated fullerene or a fullerene derivative including an ester group, and a perfluoropolyether.

Although each of Patent Document 2 (Japanese Laid-open Patent Publication No. 2011-140480), Patent Document 3 (Japanese Laid-open Patent Publication No. 2013-140923) and Patent Document 4 (Japanese Laid-open Patent Publication No. 2013-170137) discloses a fullerene derivative including one perfluoropolyether chain in a molecule as an n-type semiconductor material, its purpose to be used as a lubricant is not described.

Each of Patent Document 5 (Japanese Patent No. 5600202) and Patent Document 6 (Japanese Patent No. 5600222) discloses a lubricant composed of a derivative in which one perfluoropolyether chain is provided for each cyclopropane ring that is condensed to a fullerene.

PATENT DOCUMENTS

[Patent Document 1] Japanese Laid-open Patent Publication No. 2006-131874
[Patent Document 2] Japanese Laid-open Patent Publication No. 2011-140480
[Patent Document 3] Japanese Laid-open Patent Publication No. 2013-140923
[Patent Document 4] Japanese Laid-open Patent Publication No. 2013-170137
[Patent Document 5] Japanese Patent No. 5600202
[Patent Document 6] Japanese Patent No. 5600222

NON-PATENT DOCUMENTS

[Non-Patent Document 1] Appl. Phys. Lett. 62, 3253 (1993)
[Non-Patent Document 2] Russian Journal of Applied Chemistry 75, 1330 (2002)

When using a chemical compound including a fullerene backbone as a lubricant, there is a problem that good dispersibility cannot be obtained because fullerenes themselves aggregate, and sufficient abrasion resistance cannot be provided to an object. Further, according to Patent Document 1, as the lubricant is a mixture of a fullerene or a fullerene derivative and a perfluoropolyether, there is a problem that compatibility is insufficient and aggregation easily occurs. Thus, when a fullerene or a fullerene derivative and a perfluoropolyether are used as a lubricant at the same time, there is a problem that sufficient abrasion resistance cannot be provided to an object.

According to Patent Document 5 and Patent Document 6, in order to solve the above described problem, a fullerene derivative is suggested that includes a fullerene backbone and a perfluoropolyether chain in a molecule. A fullerene derivative is described in which one perfluoropolyether chain is introduced to each cyclopropane ring via the cyclopropane ring condensed to a fullerene backbone in a molecule. However, as the perfluoropolyether chain is a part that contributes to solubility to a fluorine series solvent that is used when coating a lubricant, and also contributes to lubricity itself, there is a problem that the fullerene derivative described in these Patent Documents is low in solubility and hardly dissolved in a perfluoroalkane (tetradecafluorohexane, for example) that is one of fluorine series solvents used for coating the lubricant composed of a perfluoropolyether chemical compound. In addition, as the fullerene derivative described in these Patent Documents is low in fluidity, there is a problem that smoothness of a lubricated surface is damaged when an object repeatedly contacts the lubricated surface to lower lubricity.

SUMMARY OF THE INVENTION

The present invention is made in light of the above problems, and provides a fullerene derivative and its purpose capable of solving the above problems.

The present invention includes the following structure.
[1] A fullerene derivative including, in a molecule,
a fullerene backbone, and
n pyrrolidine rings each being condensed to the fullerene backbone,
each of the pyrrolidine rings including one aryl group including a group including m perfluoropolyether chains, "m" being an integer from 2 to 5 and "n" being an integer from 1 to 5.

[2] The fullerene derivative according to the clause [1], wherein the fullerene derivative is a chemical compound expressed by the following general formula (1). (in the formula, "FLN" is the fullerene backbone, "A" is the group including perfluoropolyether chains, and "$R^1$" is a hydrogen atom or a hydrocarbon group whose carbon number is less than or equal to 24.)

[Chem. 1]

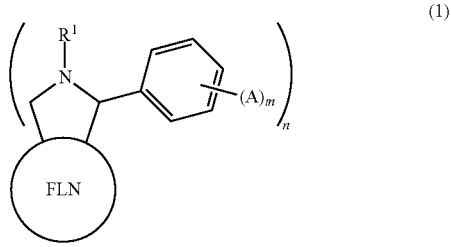

(1)

[3] The fullerene derivative according to the clause [2], wherein the "$R^1$" is an alkyl group or an aryl group whose carbon number is less than or equal to 24.
[4] The fullerene derivative according to any one of the clauses [1] to [3], wherein the fullerene backbone is $C_{60}$.
[5] The fullerene derivative according to any one of the clauses [1] to [4], wherein the group including perfluoropolyether chains includes at least a partial structure selected from —$(CF_2)_xO$— (in the formula, "x" is an integer from 1 to 5.).
[6] The fullerene derivative according to the clause [5], wherein the group including perfluoropolyether chains includes a partial structure expressed by —$(CF_2CF_2O)_y(CF_2O)_z$— (in the formula, each of "y" and "z" is an integer from 1 to 50.).
[7] The fullerene derivative according to any one of the clauses [1] to [6], wherein the group including perfluoropolyether chains is configured only by a perfluoropolyether structure.
[8] The fullerene derivative according to any one of the clauses [1] to [6], wherein the group including perfluoropolyether chains is a straight-chain.
[9] A lubricant including the fullerene derivative according to any one of the clauses [1] to [8].
[10] The lubricant according to the clause [9], further including a perfluoropolyether chemical compound that does not include a fullerene backbone.

The fullerene derivative of the invention is soluble to various fluorine series solvents such as a perfluoroalkane. Further, smoothness of a lubricated layer surface can be retained even when an object repeatedly contacts a lubricant layer.

DETAILED DESCRIPTION OF THE PREFERRED EMBODIMENTS

Figure 1:
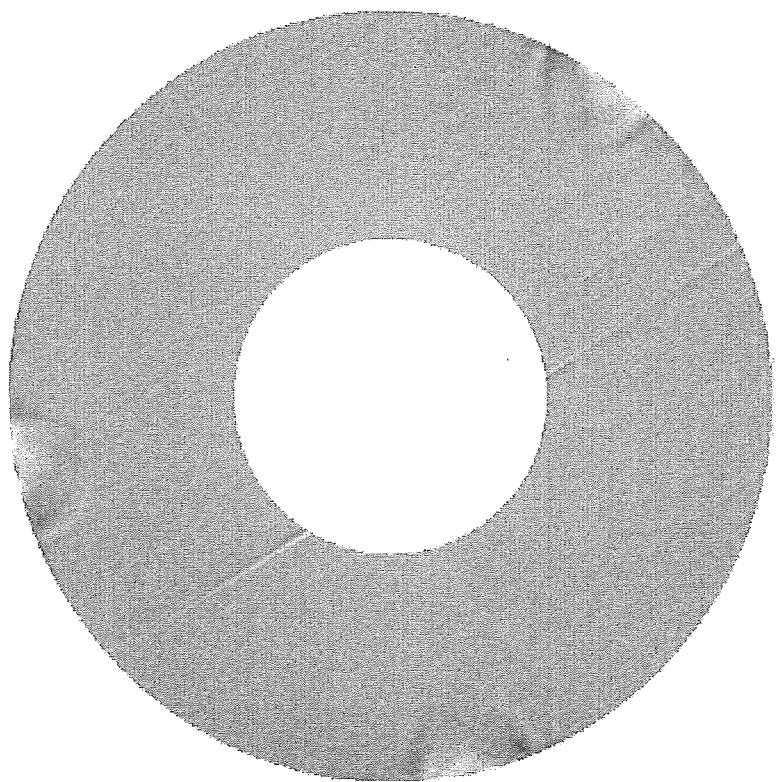
FIG. 1 is a view illustrating a coat film distribution of an example.

The structures of the invention are described in the following. It is to be understood that minor modifications may be made therein without departing from the spirit and scope of the invention as defined by the claims.

The fullerene derivative of the invention includes, in a molecule, a fullerene backbone, and n pyrrolidine rings each being condensed to the fullerene backbone, each of the pyrrolidine rings including one aryl group including a group including m perfluoropolyether chains, "m" being an integer from 2 to 5 and "n" being an integer from 1 to 5.

Further, the aryl group includes a group including 2 to 5 perfluoropolyether chains, preferably 2 to 3 perfluoropolyether chains. Within such a range, it can be considered that a ratio of a perfluoropolyether chain part with respect to a fullerene part in a molecule becomes appropriate, and lubricity of a lubricant using the fullerene derivative of the invention can be easily increased, and smoothness of a lubricant layer can be easily retained.

Further, it is preferable that the perfluoropolyether chain includes at least one partial structure selected from —$(CF_2)_xO$— (in the formula, "x" is an integer from 1 to 5.). When the perfluoropolyether chain includes such a partial structure, compared with a chemical compound that does not include such a partial structure, solubility to a fluorine series solvent is increased, and as a result, it can be more uniformly coated on a surface of a coating surface. Further, among various perfluoropolyether chains, a perfluoropolyether chain in which "x" is 1 to 3 is industrially manufactured, easily available, and industrially easily used.

Further, it is more preferable that the perfluoropolyether chain includes a partial structure expressed by —$(CF_2CF_2O)_y(CF_2O)_z$—. Here, each of "y" and "z" is an integer from 1 to 50. Further, it is preferable that the formula weight of the partial structure expressed by —$(CF_2CF_2O)_y(CF_2O)_z$— is within a range of 300 to 6000, preferably, within a range of 500 to 6000, and more preferably, within a range of 600 to 3000. When including such a structure, lubricity and solubility to a fluorine series solvent are improved.

Here, the fullerene may be bonded at either directions of the partial structure expressed by —$(CF_2)_xO$— or —$(CF_2CF_2O)_y(CF_2O)_z$—.

Although structures in the group including perfluoropolyether chains, other than the perfluoropolyether chains, are not specifically limited, as a structure of a connection portion of the aryl group and the perfluoropolyether chains, for example, a structure including an ether bond or an ester bond may be exemplified. Further, as a structure of an end portion of the group including perfluoropolyether chains, for example, a structure including a perfluoroalkyl group such as a trifluoromethyl group or a perfluorobutyl group, an alkyl group such as a methyl group or a butyl group, an aryl group such as a phenyl group or a naphthyl group, an aralkyl group such as a benzyl group or a phenylpropyl group or an aryloyl group such as a benzoyl group or a naphthoyl group may be exemplified. Among them, a structure that includes a perfluoroalkyl group or an aryl group at an end is preferable, and in particular, for the former case, a perfluorobutyl group, for the latter case, a phenyl group, a naphthyl group, a benzoyl group or a naphthoyl group is preferable.

Although the aryl group to which the group including perfluoropolyether chains is bonded is not specifically limited, for example, a phenyl group, a naphthyl group, a pyridyl group, a thienyl group or a furyl group is exemplified, and among them, a phenyl group is preferable.

As the fullerene backbone of the fullerene derivative of the invention, for example, $C_{60}$, $C_{70}$, $C_{76}$, $C_{78}$, further high-order fullerene or the like is exemplified, and among them, $C_{60}$ is preferable. As it is industrially easy to obtain $C_{60}$ of high purity compared with other types of fullerenes, purity of the fullerene derivative derived from $C_{60}$ as a source material can be made high as well, and good lubricity and smoothness can be obtained.

As a specific example of the fullerene derivative, a chemical compound expressed by the following general formula (1) may be used.

[Chem. 2]

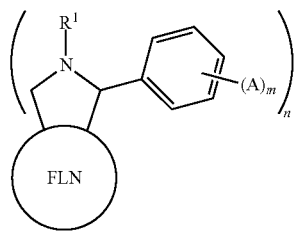

(1)

(in the formula, "FLN" is the fullerene backbone, "A" is the group including perfluoropolyether chains, and "$R^1$" is a hydrogen atom or a hydrocarbon group whose carbon number is less than or equal to 24.)

"$R^1$" in the general formula (1) is a hydrogen atom or a hydrocarbon group whose carbon number is 1 to 24, and as a hydrocarbon group, for example, an alkyl group such as a methyl group or an ethyl group, an aryl group such as a phenyl group or a naphthyl group or an aralkyl group such as a benzyl group or a phenylpropyl group is exemplified. Among them, an alkyl group or an aryl group is preferable, and a methyl group or a phenyl group is particularly preferable.

(Lubricant)

The lubricant of the invention includes the fullerene derivative of the invention. The lubricant may solely use the fullerene derivative of the invention, or a perfluoropolyether chemical compound that does not include a fullerene backbone may be used at the same time by adding it to the fullerene derivative of the invention. Although the perfluoropolyether chemical compound that does not include a fullerene backbone is not specifically limited, for example, a perfluoropolyether chemical compound that is conventionally known as a lubricant may be used. As such a chemical compound, for example, FOMBLIN (registered trademark) series (manufactured by Solvay Specialty Polymers) or the like are exemplified.

As the fullerene derivative of the invention includes perfluoropolyether chains in a molecule, the fullerene derivative of the invention has a good compatibility with a perfluoropolyether chemical compound. Thus, even when the lubricant includes the fullerene derivative of the invention and the perfluoropolyether chemical compound that does not include a fullerene backbone at the same time, the fullerene derivative of the invention can be uniformly dispersed or dissolved in the lubricant.

Further, when the lubricant includes the fullerene derivative of the invention and the perfluoropolyether chemical compound that does not include a fullerene backbone at the same time, it is preferable that the content of the fullerene derivative of the invention in the lubricant is greater than or equal to 0.1 mass %, more preferably, greater than or equal to 1 mass %, and particularly preferably, greater than or equal to 10 mass % for actualizing good adsorptivity to a coating surface.

(Method of Manufacturing Fullerene Derivative of Invention)

The fullerene derivative of the invention may be manufactured in accordance with the following two types of synthesizing methods.

The fullerene derivative expressed by the general formula (1) may be obtained by, for example, an addition reaction in which a fullerene, an amino acid expressed by $R^1$—NH—$CH_2$—COOH ("$R^1$" is a hydrogen atom or a hydrocarbon group whose carbon number is 1 to 24 and same as that of the general formula (1)) and a benzaldehyde derivative expressed by the following general formula (2) (in the formula, "A" is a group including perfluoropolyether chains and "m" is an integer from 2 to 5 and same as that of the general formula (1)) are starting materials.

[Chem. 3]

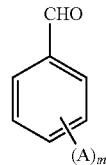

(2)

This reaction can be conducted in a solvent. The solvent is not specifically limited as long as the solvent can dissolve the fullerene, the amino acid expressed by $R^1$—NH—$CH_2$—COOH and the benzaldehyde derivative expressed by the general formula (2). For example, a mixed solvent of an aromatic series solvent such as toluene, xylene or orthodichlorobenzene capable of dissolving the fullerene, and a fluorine series solvent such as hexafluorobenzene, AK-225 (manufactured by Asahi Glass Co., Ltd) or hexafluorotetrachlorobutane may be exemplified.

It is preferable that the reaction is conducted under inert gas atmosphere while heating and stirring. By conducting the reaction under inert gas atmosphere, generation of a by-product can be suppressed. Further, heating may be performed at greater than or equal to 40° C. and less than or equal to 200° C. When the reaction is conducted at less than or equal to 40° C., it is not preferable because sufficient reaction rate cannot be obtained and reaction time becomes longer. On the other hand, when the reaction is conducted at greater than or equal to 200° C., it is not preferable because a side reaction proceeds and yield is lowered.

After cooling the reaction mixture to room temperature, the reaction solvent is evaporated by an evaporator. Then, the obtained mixture is dissolved in a fluorine series solvent such as AK-225, and filtered to remove impurities such as an unreacted fullerene. Then, by evaporating the solvent again, a crude product is obtained.

In addition to the above described method, the fullerene derivative expressed by the general formula (1) may be synthesized by an ester exchange reaction in which a fullerene derivative including a carboxylate structure expressed by a general formula (3) (in the formula, "$R^1$" is a hydrogen atom or a hydrocarbon group whose carbon number is 1 to 24 and same as that of the general formula (1)). "$R^2$" is a methyl group or an ethyl group. "m" is an integer from 2 to 5, "n" is an integer from 1 to 5, and same as those of the general formula (1)) is a starting material. The fullerene derivative expressed by the general formula (3) may be obtained by, for example, an addition reaction in which a fullerene, an amino acid expressed by $R^1$—NH—$CH_2$—

COOH and a benzaldehyde derivative including an ester group expressed by a general formula (4) (in the formula, "$R^2$" is a methyl group or an ethyl group and "m" is an integer from 2 to 5, and same as those of the general formula (3)) are starting materials.

[Chem. 4]

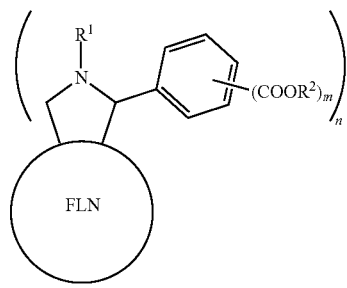

(3)

[Chem. 5]

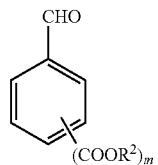

(4)

The fullerene derivative expressed by the general formula (1) can be obtained by an ester exchange reaction of an alcohol including a perfluoropolyether structure to the fullerene derivative expressed by the general formula (3) in the presence of an acid catalyst. In the reaction, as the acid catalyst, a generally known inorganic acid or an organic acid may be used. For example, a hydrochloric acid, a sulfuric acid, a p-toluenesulfonic acid, a trifluoromethanesulfonic acid or the like may be exemplified. In the reaction, as the alcohol including the perfluoropolyether structure, an industrially manufactured chemical compound may be used. For example, FOMBLIN (registered trademark) series (manufactured by Solvay Specialty Polymers) or the like may be exemplified.

This reaction can be conducted in a solvent. The solvent is not specifically limited as long as the solvent can dissolve the fullerene derivative expressed by the general formula (3) and the alcohol derivative including the perfluoropolyether structure. For example, a mixed solvent of aromatic series solvent such as toluene, xylene or orthodichlorobenzene capable of dissolving the fullerene derivative and a fluorine series solvent such as hexafluorobenzene, AK-225 (manufactured by Asahi Glass Co., Ltd) hexafluorotetrachlorobutane may be exemplified.

It is preferable that the reaction is conducted under inert gas atmosphere while heating and stirring. By conducting the reaction under inert gas atmosphere, generation of a by-product can be suppressed. Further, it is preferable that the reaction is conducted by attaching a Soxhlet extractor in which a cylindrical filter paper made of a glass fiber and molecular sieves are provided, heating to temperature that exceeds a boiling point of the used solvent and refluxing the solvent. By removing methanol or ethanol that is generated as a by-product from a reaction system as such, the ester exchange reaction can be efficiently proceeded.

After cooling the reaction mixture to room temperature, and appropriately neutralizing, the reaction solvent is evaporated by a rotary evaporator. Then, the obtained mixture is dissolved in a fluorine series solvent such as AK-225, and filtered to remove impurities such as an unreacted fullerene or a fullerene derivative. Then, by evaporating the solvent again, a crude product is obtained.

The crude products obtained by the above described two types of methods can be used as lubricants as they are, respectively. If higher purity is required, for example, the crude product can be further purified by supercritical fluid extraction (SFE) with carbon dioxide. Specifically, the crude product is introduced in a pressure container, and by introducing liquefied carbon dioxide into the container while keeping the pressure and the temperature in the container, the carbon dioxide is made into a supercritical fluid state and a targeted chemical compound can be obtained by extraction.

It is preferable that the temperature in the container is greater than or equal to 31° C. and less than or equal to 80° C. If the temperature is less than 31° C., the carbon dioxide is not made into a supercritical state, and if the temperature exceeds 80° C., extraction property of the supercritical carbon dioxide becomes weak. Further, it is preferable that the pressure at this time is greater than or equal to 7.38 MPa and less than or equal to 30 MPa. If the pressure is less than 7.38 MPa, the carbon dioxide is not made into a supercritical state, and if the pressure exceeds 30 MPa, pressure resistance property is required for the apparatus and price of the apparatus becomes high, and as a result, manufacturing cost becomes high.

When an end portion of the group including perfluoropolyether chains expressed by "A" of the fullerene derivative expressed by the general formula (1) obtained by the above described method at an opposite side of a direction at which the fullerene backbone is bonded is an exchangeable structure such as a hydroxyl group or a carboxyl group, the structure can be exchanged by conducting a known reaction to the fullerene derivative. The crude product of the exchange reaction can be used as a lubricant as it is. If higher purity is required, for example, the crude product can be further purified by supercritical fluid extraction (SFE) with carbon dioxide.

The lubricant of the invention may be used as, for example, a lubricant for a magnetic recording medium (a hard disk or the like). Although a step of coating the lubricant on a surface of the magnetic recording medium is not specifically limited, for example, spin coating, dipping or the like may be used. When coating the lubricant on the magnetic recording medium by dipping, for example, a method of coating a lubricant layer on a surface of the magnetic recording medium by immersing the magnetic recording medium in a lubricant solution provided in a dipping bath of a dip coat apparatus, and thereafter drawing up the magnetic recording medium from the dipping bath at a predetermined speed. The lubricant solution includes the fullerene derivative, and it is preferable that the concentration of the fullerene derivative is greater than or equal to 0.001 mass %.

EXAMPLES

The present invention is specifically described based on examples in the following. However, the present invention is not limited to those examples.
(NMR Analysis)
$^1$H-NMR was measured by the following conditions.
Apparatus: JNM-EX270, manufactured by JEOL Ltd.

Sample preparation: after dissolving a sample (approximately 10 mg to 30 mg) in a CDCl$_3$/hexafluorobenzene mixed solvent (approximately 0.5 mL), the sample was introduced in an NMR sample tube whose diameter was 5 mm.

Measured temperature: room temperature

Reference material: a signal of tetramethylsilane added in the solvent was used as reference.

(Measurement of Thickness of Lubricant Layer)

The thickness of the lubricant layer was obtained by intensity of an absorption peak corresponding to a stretching vibration energy of a C—F bond in an infrared absorption spectrum. Four points were measured for each lubricant layer, and an average value was determined to be its thickness.

Apparatus: Nicolet iS50, manufactured by Thermo Fisher Scientific Inc.

Measurement method: reflection absorption spectroscopy (Smoothness Evaluation of Lubricant Layer Against Repeated Friction)

Smoothness evaluation of the lubricant layer against repeated friction was conducted by using an SAF tester manufactured by Kubota Corporation. Specifically, while rotating a hard disk on which the lubricant was coated at 12000 rpm, load and subsequent unload of a head on a same radius of a disk surface was repeated for 20,000 times at a speed of once/three seconds. Thereafter, the surface of the disk was observed by an optical microscope, and whether a passing trail of the head exists or not was confirmed.

(Evaluation of Smoothness by Optical Surface Analysis of Lubricant Coat Film)

Thickness distribution of a surface was observed using an optical surface analyzer.

Synthetic Example 1

[Formula 1]

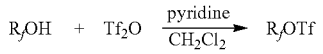

(5)

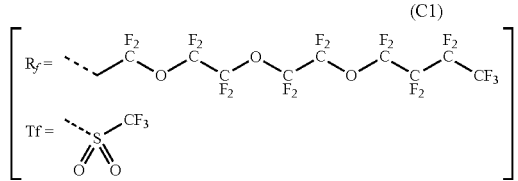

Synthesis of Chemical Compound 1 (C1):

Fluorinated triethylene glycol monobutyl ether (manufactured by Exfluor Research Corporation, 13 g, 24 mmol) and pyridine (2.3 g, 29 mmol) were added to dichloromethane (120 mL), and dichloromethane (120 mL) solution of trifluoromethanesulfonic anhydride (8.2 g, 29 mmol) was dropped to the obtained solution. After stirring at room temperature for 16 hours, the reaction mixture was washed once by each of pure water (100 mL) and saturated sodium carbonate aqueous solution (100 mL). After filtering the obtained organic layer and condensing it by a rotary evaporator, fluorinated triethylene glycol monobutyl ether trifluoromethanesulfonic acid ester (a chemical compound 1) (15 g, 22 mmol, yield 92%) was obtained as a lemon yellow oily material. The crude product was used in a subsequent reaction without purification.

Synthetic Example 2

[Formula 2]

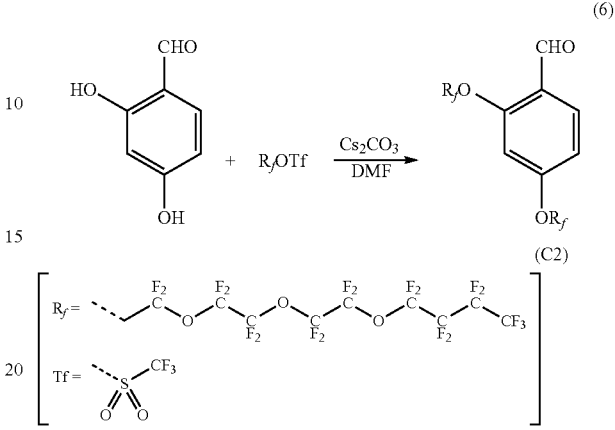

Synthesis of Chemical Compound 2 (C2):

The chemical compound 1 obtained by the synthetic example 1 (4.5 g, 6.6 mmol) and 2,4-dihydroxybenzaldehyde (0.41 g, 3.0 mmol) were added to N,N-dimethylformamide (30 mL), and cesium carbonate (2.9 g, 9.0 mmol) was added to the obtained solution. After stirring at 70° C. for one hour, the reaction mixture was cooled to room temperature, and condensed by a rotary evaporator. The obtained mixture was separated by using pure water (30 mL) and AK-225 (30 mL), and an aqueous layer was extracted twice by AK-225 (20 mL). The obtained organic layer was water washed and dried by magnesium sulfate. After filtering and condensing it by a rotary evaporator, a rufous oily crude product (3.8 g) was obtained. By purified by silica gel column chromatography (developing solvent: hexane-ethyl acetate (9:1)), 2,4-dialkoxybenzaldehyde (a chemical compound 2) was obtained as a lemon yellow oily material (3.4 g, 2.8 mmol, yield 95%).

Synthetic Example 3

[Formula 3]

(7)

11

-continued

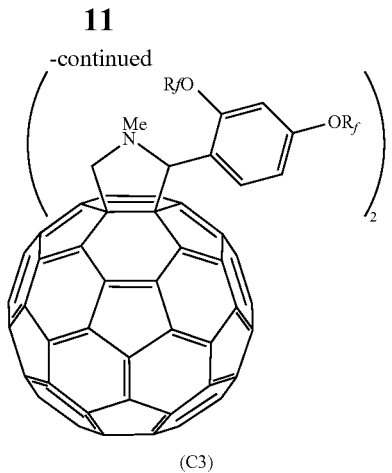

(C3)

[HFTCB = hexafluorotetrachlorobutane]

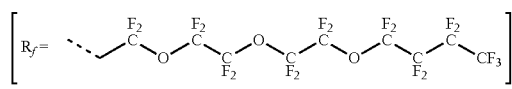

Synthesis of Chemical Compound 3 (C3):

The chemical compound 2 obtained by the synthetic example 2 (3.4 g, 2.8 mmol) and N-methylglycine (2.2 g, 25 mmol) were added to hexafluorotetrachlorobutane (30 mL), and orthodichlorobenzene (60 mL) solution of $C_{60}$ fullerene (1.0 g, 1.4 mol) was rapidly added to the obtained mixture. A Dimroth condenser was attached, and the mixture was heated by a hot water bath set at 160° C. and refluxed for 3 hours while stirring. After condensing the reaction mixture cooled to room temperature by a rotary evaporator, the reaction mixture was dissolved in an appropriate amount of AK-225 and filtered. The obtained solution was washed by pure water (50 mL) and dried by magnesium sulfate. After filtering and condensing it by a rotary evaporator, a black oily crude product (4.0 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 9 to 12 MPa, a by-product in which three or more pyrrolidine rings were formed on the fullerene backbone was removed by extraction. Thereafter, the pressure was raised to 20 MPa, and 3.4 g of a russet solid (a chemical compound 3) was extracted. Under this condition, a derivative having one pyrrolidine ring was not extracted. This solid was confirmed as the above described chemical compound by the following analysis result of NMR.

$^1$H-NMR δ (ppm): 2.93 (brs, 6H), 4.44 (br, 14H), 6.52-6.66 (m, 2H), 6.69-6.85 (m, 4H).

12

Synthetic Example 4

[Formula 4]

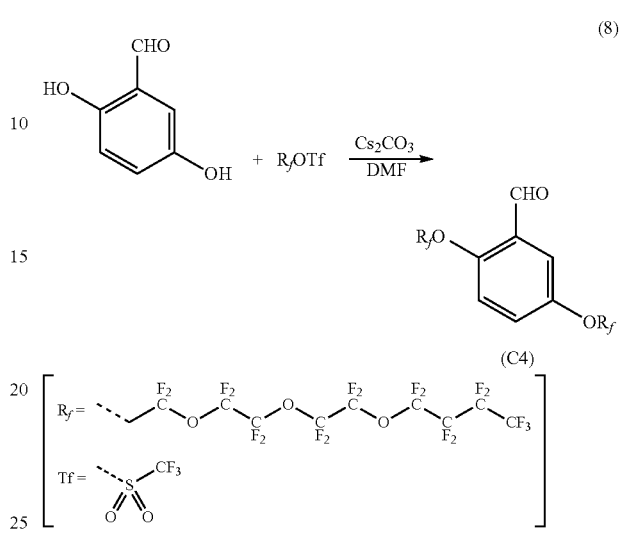

Synthesis of Chemical Compound 4 (C4):

The chemical compound 1 obtained by the synthetic example 1 (4.5 g, 6.6 mmol) and 2,5-dihydroxybenzaldehyde (0.41 g, 3.0 mmol) were added to N,N-dimethylformamide (30 mL), and cesium carbonate (2.9 g, 9.0 mmol) was added to the obtained solution. After stirring at 70° C. for one hour, the reaction mixture was cooled to room temperature, and condensed by a rotary evaporator. The obtained mixture was separated by using pure water (30 mL) and AK-225 (30 mL), and an aqueous layer was extracted twice by AK-225 (20 mL). The obtained organic layer was water washed and dried by magnesium sulfate. After filtering and condensing it by a rotary evaporator, a rufous oily crude product (3.1 g) was obtained. By purified by silica gel column chromatography (developing solvent: hexane-ethyl acetate (9:1)), 2,5-dialkoxybenzaldehyde (a chemical compound 4) was obtained as a lemon yellow solid (2.3 g, 1.9 mmol, yield 65%).

Synthetic Example 5

[Formula 5]

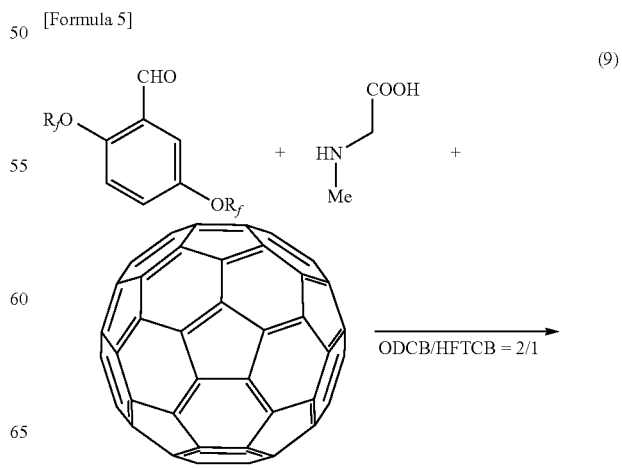

-continued

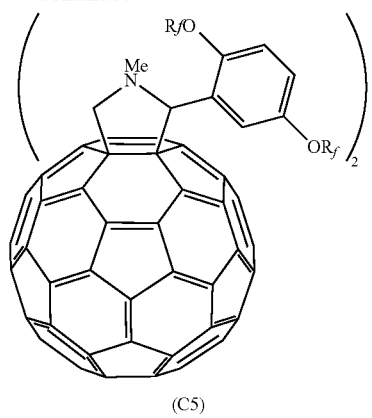

(C5)

[HFTCB = hexafluorotetrachlorobutane]

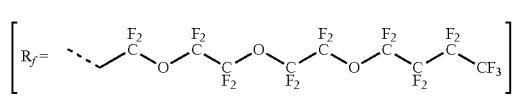

Synthesis of Chemical Compound 5 (C5):

The chemical compound 4 obtained by the synthetic example 4 (2.3 g, 1.9 mmol) and N-methylglycine (1.6 g, 18 mmol) were added to hexafluorotetrachlorobutane (30 mL), and orthodichlorobenzene (60 mL) solution of $C_{60}$ fullerene (0.75 g, 1.0 mmol) was rapidly added to the obtained mixture. A Dimroth condenser was attached, and the mixture was heated by a hot water bath set at 160° C. and refluxed for 3 hours while stirring. After condensing the reaction mixture cooled to room temperature by a rotary evaporator, the reaction mixture was dissolved in an appropriate amount of AK-225 and filtered. The obtained solution was washed by pure water (50 mL) and dried by magnesium sulfate. After filtering and condensing it by a rotary evaporator, a black oily crude product (1.8 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 9 to 12 MPa, a by-product in which three or more pyrrolidine rings were formed on the fullerene backbone was removed by extraction. Thereafter, the pressure was raised to 20 MPa, and 1.6 g of a russet solid (a chemical compound 5) was extracted. Under this condition, a derivative having one pyrrolidine ring was not extracted. This solid was confirmed as the above described chemical compound by the following analysis result of NMR.

$^1$H-NMR δ (ppm): 2.75 (brs, 6H), 4.36 (br, 14H), 6.52-6.63 (m, 2H), 6.72-6.85 (m, 4H).

Synthetic Example 6

[Formula 6]

(10)

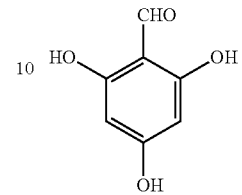

+ R$_f$OTf $\xrightarrow{Cs_2CO_3}{DMF}$

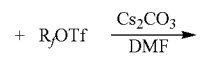

(C6)

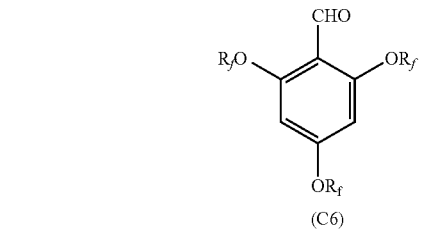

Synthesis of Chemical Compound 6 (C6):

The chemical compound 1 obtained by the synthetic example 1 (6.5 g, 10 mmol) and 2,4,6-trihydroxybenzaldehyde (0.47 g, 3.0 mmol) were added to N,N-dimethylformamide (60 mL), and cesium carbonate (4.4 g, 14 mmol) was added to the obtained solution. After stirring at 70° C. for two hours, the reaction mixture was cooled to room temperature, and condensed by a rotary evaporator. The obtained mixture was separated by pure water (30 mL) and AK-225 (30 mL), and an aqueous layer was extracted twice by AK-225 (20 mL). The obtained organic layer was water washed and dried by magnesium sulfate. After filtering and condensing it by a rotary evaporator, a rufous oily crude product (5.2 g) was obtained. By purified by silica gel column chromatography (developing solvent: hexane-ethyl acetate (9:1)), 2,4,6-trialkoxybenzaldehyde (a chemical compound 6) was obtained as a lemon yellow oily material (4.4 g, 2.5 mmol, yield 83%).

Synthetic Example 7

[Formula 7]

(11)

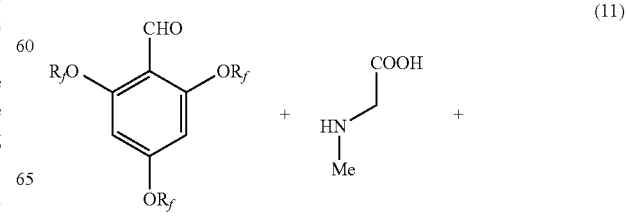

15

-continued

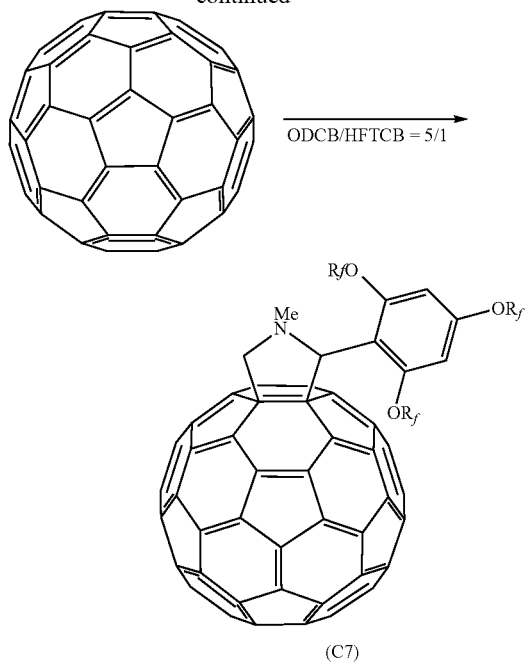

(C7)

[HFTCB = hexafluorotetrachlorobutane]

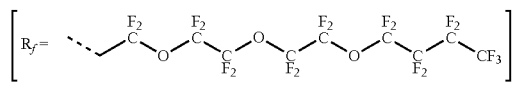

Synthesis of Chemical Compound 7 (C7):

The chemical compound 6 obtained by the synthetic example 6 (4.4 g, 2.5 mmol) and N-methylglycine (2.0 g, 23 mmol) were added to hexafluorotetrachlorobutane (20 mL), and orthodichlorobenzene (40 mL) solution of $C_{60}$ fullerene (1.9 g, 2.6 mmol) was rapidly added to the obtained mixture. A Dimroth condenser was attached, and the mixture was heated by a hot water bath set at 160° C. and refluxed for 4 hours while stirring. After condensing the reaction mixture cooled to room temperature by a rotary evaporator, the reaction mixture was dissolved in an appropriate amount of AK-225 and filtered. The obtained solution was washed by pure water (50 mL) and dried by magnesium sulfate. After filtering and condensing it by a rotary evaporator, a black oily crude product (5.4 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 15 to 20 MPa, a by-product in which two or more pyrrolidine rings were formed on the fullerene backbone was removed by extraction. Thereafter, the pressure was raised to 22 MPa, and 1.4 g of a russet solid (a chemical compound 7) was extracted. This solid was confirmed as the above described chemical compound by the following analysis result of NMR.

$^1$H-NMR δ (ppm): 2.85 (s, 3H), 4.20 (d, 1H), 4.44 (t, 4H), 4.62 (t, 2H), 5.01 (d, 1H), 5.76 (s, 1H), 6.39 (s, 2H).

16

Synthetic Example 8

[Formula 8]

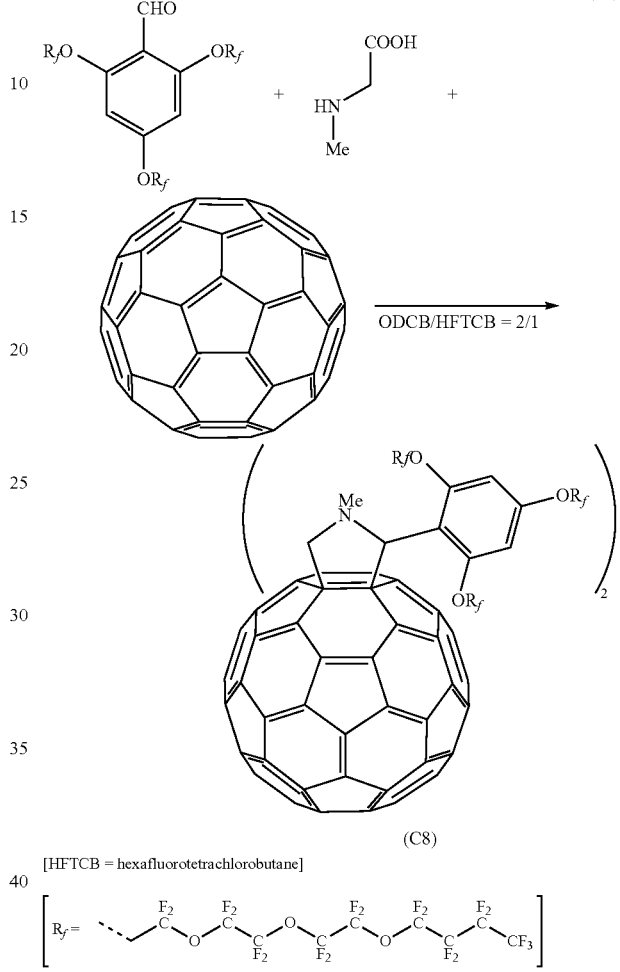

(C8)

[HFTCB = hexafluorotetrachlorobutane]

Synthesis of Chemical Compound 8 (C8):

The chemical compound 6 obtained by the synthetic example 6 (1.7 g, 1.0 mmol) and N-methylglycine (0.80 g, 9.0 mmol) were added to hexafluorotetrachlorobutane (20 mL), and orthodichlorobenzene (100 mL) solution of $C_{60}$ fullerene (0.36 g, 0.50 mmol) was rapidly added to the obtained mixture. A Dimroth condenser was attached, and the mixture was heated by a hot water bath set at 160° C. and refluxed for 20 hours while stirring. After condensing the reaction mixture cooled to room temperature by a rotary evaporator, the reaction mixture was dissolved in an appropriate amount of AK-225 and filtered. The obtained solution was washed by pure water (50 mL) and dried by magnesium sulfate. After filtering and condensing it by a rotary evaporator, a black oily crude product (2.1 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 9 to 12 MPa, a by-product in which three or more pyrrolidine rings were formed on the fullerene backbone was removed by extraction. Thereafter, the pressure was raised to 15 MPa, and 1.3 g of a black oily material (a chemical compound 8) was extracted. Under this condition, a derivative having one pyrrolidine ring was not extracted. This material was confirmed as the above described chemical compound by the following analysis result of NMR.

$^1$H-NMR δ (ppm): 2.79 (brs, 6H), 4.39 (br, 18H), 6.22 (brs, 4H).

Synthetic Example 9

[Formula 9]

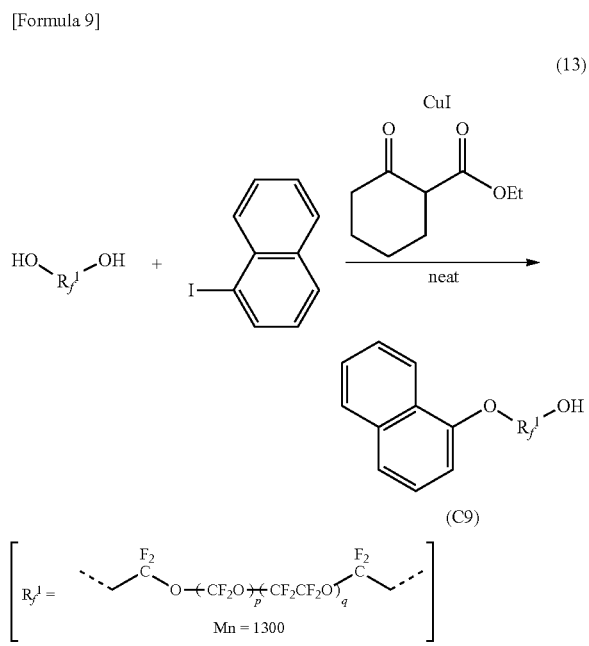

Synthesis of Chemical Compound 9 (C9):

FOMBLIN ZDOL whose number average molecular weight (Mn) was approximately 1300 (manufactured by Solvay Specialty Polymers, 7.8 g, 6 mmol), copper (I) iodide (0.18 g, 0.95 mmol), 2-ethyl 2-oxocyclohexanecarboxylate (0.31 g, 1.8 mmol) and 1-Iodonaphthalene (2.3 g, 9.0 mmol) were mixed, and while stirring without adding a solvent, cesium carbonate (4.9 g, 15 mmol) was added. After stirring at 100° C. for 20 hours, the reaction mixture was separated by diluted hydrochloric acid (50 mL) and AK-225 (50 mL), and an aqueous layer was extracted twice by AK-225 (50 mL). After water washing the obtained organic layer, the obtained organic layer was dried by adding magnesium sulfate. After filtering and condensing it by a rotary evaporator, a crude product (8.1 g) was obtained as a fulvous oily material. By purified by silica gel column chromatography (developing solvent: hexane-ethyl acetate (9:1 to 3:1)), FOMBLIN (a chemical compound 9) including a naphthyl ether structure at one of end portions was obtained as a colorless oily material (3.0 g, 2.1 mmol, yield 35%).

Synthetic Example 10

[Formula 10]

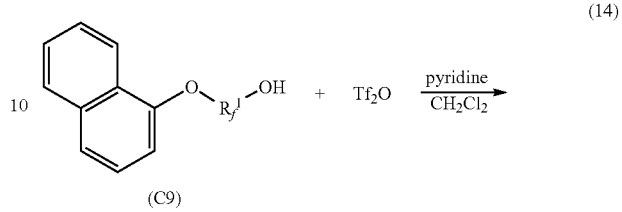
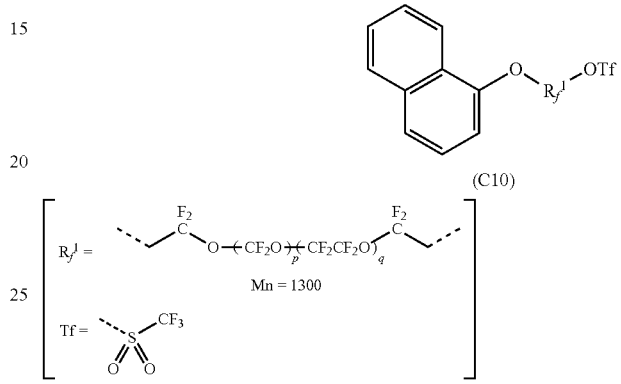

Synthesis of Chemical Compound 10 (C10):

The chemical compound 9 obtained by the synthetic example 9 (2.6 g, 1.9 mmol) and pyridine (0.22 g, 2.7 mmol) were added to AK-225 (20 mL), and AK-225 (20 mL) solution of trifluoromethanesulfonic anhydride (0.8 g, 2.8 mmol) was dropped to the obtained solution. After stirring at room temperature for one hour, the reaction mixture was washed once by each of pure water (100 mL) and saturated sodium carbonate aqueous solution (100 mL). After filtering the obtained organic layer, trifluoromethanesulfonic acid ester including a FOMBLIN structure (a chemical compound 10)(2.5 g, 1.6 mmol, yield 84%) was obtained as a colorless oily material. This crude product was used in a subsequent reaction without purification.

Synthetic Example 11

[Formula 11]

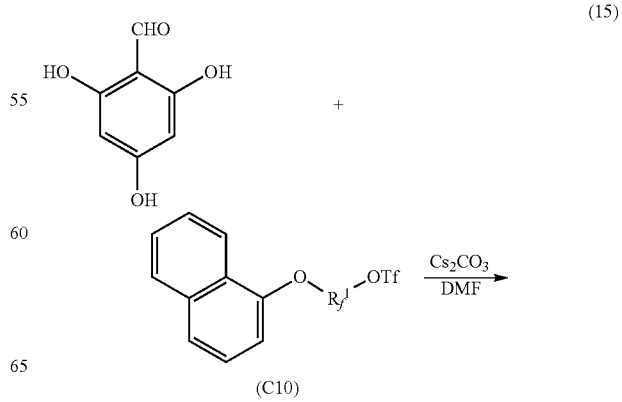

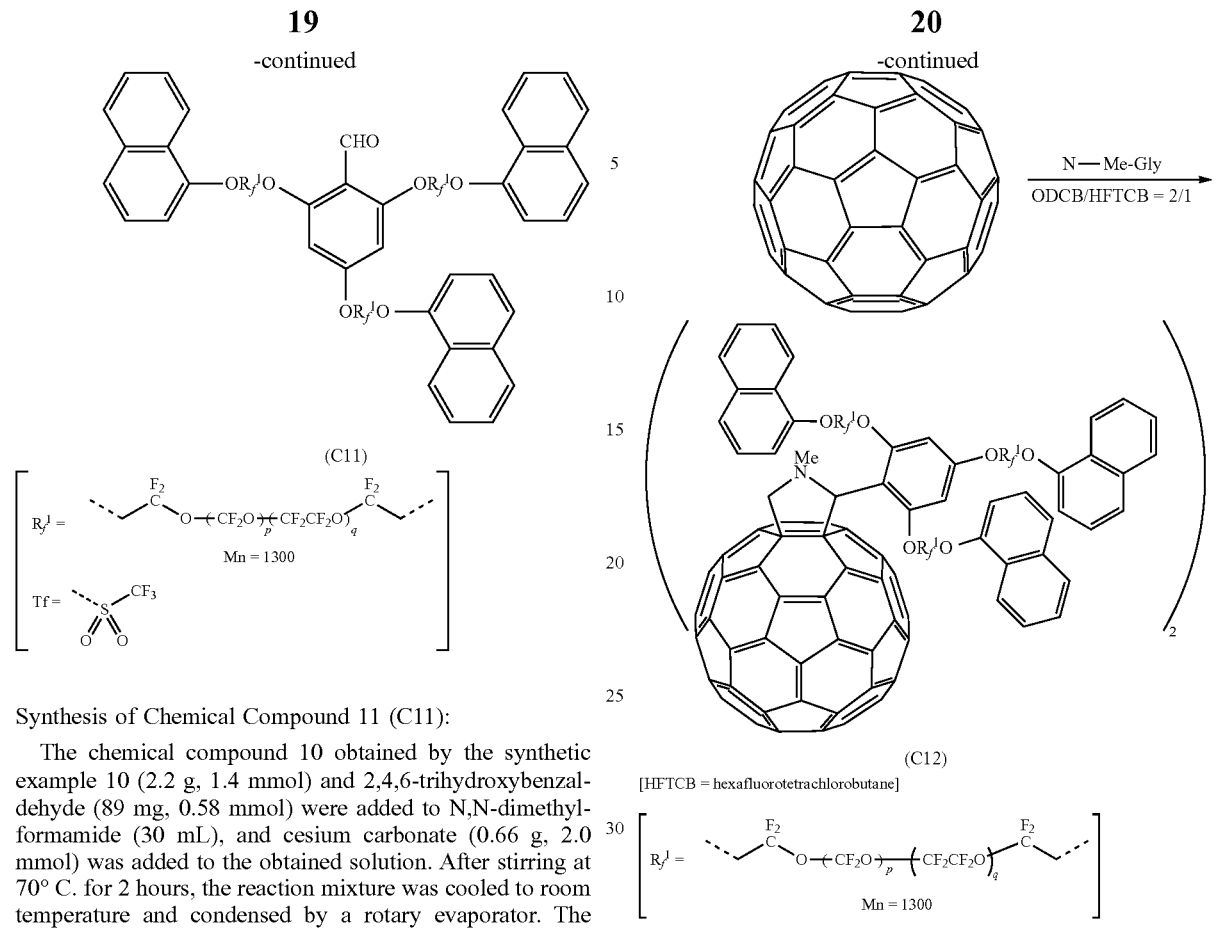

(C11)

Synthesis of Chemical Compound 11 (C11):

The chemical compound 10 obtained by the synthetic example 10 (2.2 g, 1.4 mmol) and 2,4,6-trihydroxybenzaldehyde (89 mg, 0.58 mmol) were added to N,N-dimethylformamide (30 mL), and cesium carbonate (0.66 g, 2.0 mmol) was added to the obtained solution. After stirring at 70° C. for 2 hours, the reaction mixture was cooled to room temperature and condensed by a rotary evaporator. The obtained mixture was separated by pure water (20 mL) and AK-225 (20 mL), and an aqueous layer was extracted twice by AK-225 (20 mL). The obtained organic layer was water washed and dried by magnesium sulfate. After filtering and condensing it by a rotary evaporator, a rufous oily crude product (2.9 g) was obtained. By purified by silica gel column chromatography (developing solvent: hexane-ethyl acetate (17:3)), 2,4,6-trialkoxybenzaldehyde (a chemical compound 11) was obtained as a colorless oily material (1.5 g, 0.35 mmol, yield 61%).

Synthetic Example 12

[Formula 12]

(16)

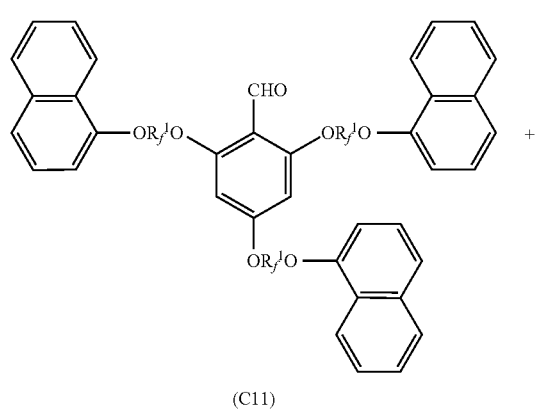

(C11)

(C12)

[HFTCB = hexafluorotetrachlorobutane]

Synthesis of Chemical Compound 12 (C12):

The chemical compound 11 obtained by the synthetic example 11 (1.5 g, 0.35 mmol) and N-methylglycine (0.30 g, 3.3 mmol) were added to hexafluorotetrachlorobutane (15 mL), and orthodichlorobenzene (30 mL) solution of $C_{60}$ fullerene (0.25 g, 0.34 mmol) was rapidly added to the obtained mixture. A Dimroth condenser was attached, and the mixture was heated by a hot water bath set at 180° C. and refluxed for 3 hours while stirring. After condensing the reaction mixture cooled to room temperature by a rotary evaporator, the reaction mixture was dissolved in an appropriate amount of AK-225 and filtered. The obtained solution was washed by pure water (50 mL) and dried by magnesium sulfate. After filtering and condensing it by a rotary evaporator, a black oily crude product (0.45 g) was obtained.

Next, the crude product was introduced in a thickness stainless container having an inlet and an outlet (inner diameter 20 mm×depth 200 mm), and while retaining temperature in the container at 60° C., using a supercritical carbon dioxide liquid feeding pump (manufactured by JASCO Corporation, PU2086-CO2), supercritical carbon dioxide was fed into the container at a liquefied carbon dioxide reduced flow rate of 5 mL/min. By varying the pressure in the container within a range of 9 to 19 MPa, a by-product in which three or more pyrrolidine rings were formed on the fullerene backbone was removed by extraction. Thereafter, the pressure was raised to 24 MPa, and 0.20 g of a black oily material (a chemical compound 12) was extracted. Under this condition, a derivative having one pyrrolidine ring was not extracted. This material was confirmed as the above described chemical compound by the following analysis result of NMR.

$^1$H-NMR δ (ppm): 2.76 (brs, 6H), 4.32 (brq, 12H), 4.46 (brq, 12H), 6.20 (brd, 6H), 6.67 (brd, 6H), 7.17 (brd, 6H), 7.49 (brs, 12H), 7.93 (brd, 6H), 8.25 (brd, 6H).

Synthetic Example 13

[Formula 13]

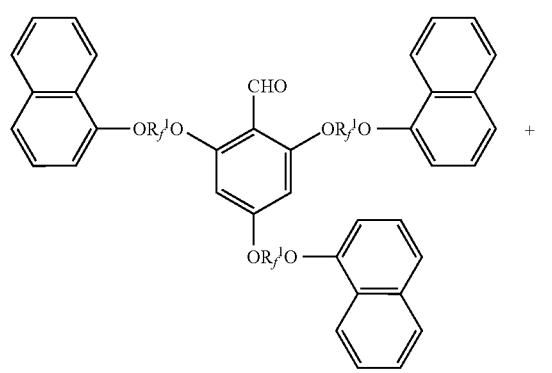

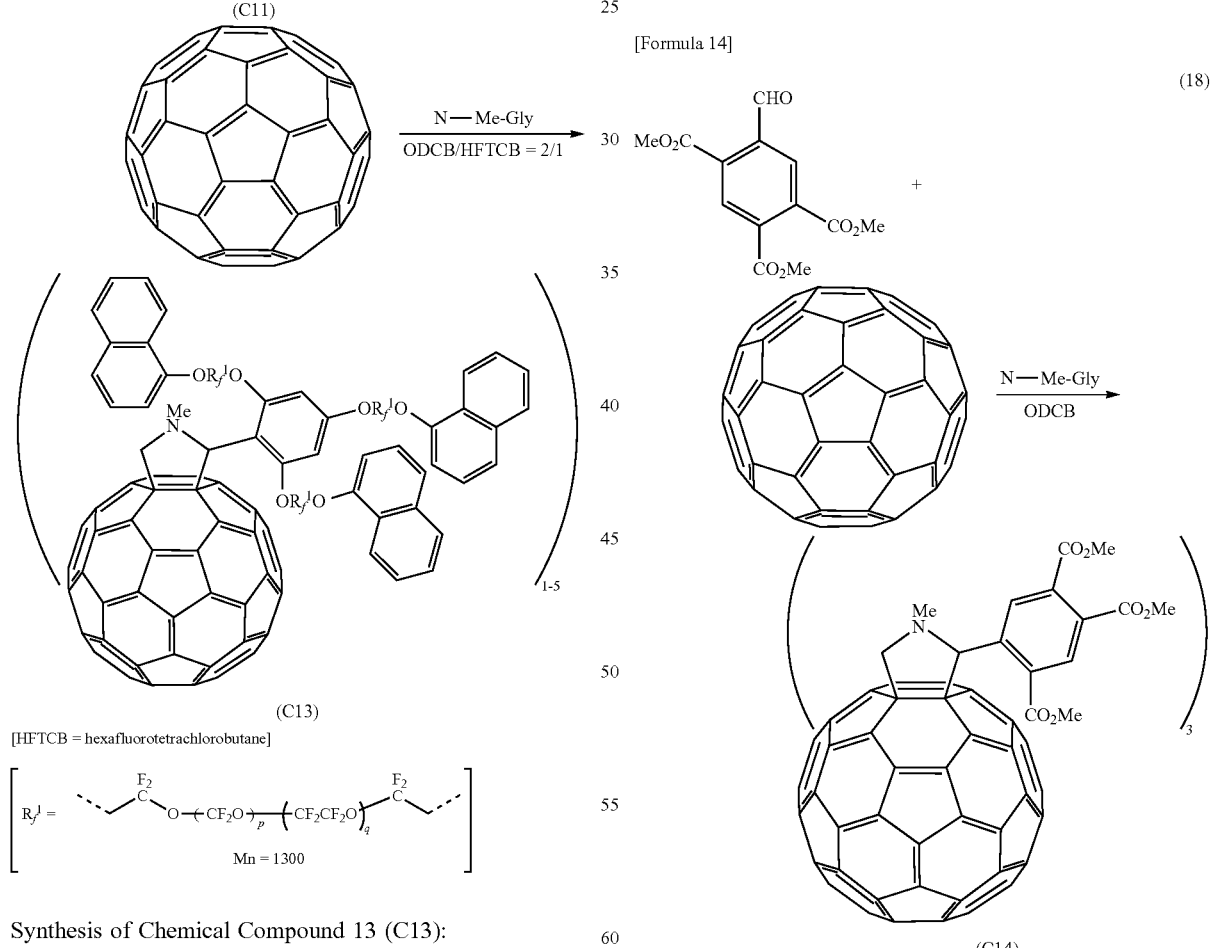

[HFTCB = hexafluorotetrachlorobutane]

Synthesis of Chemical Compound 13 (C13):

The chemical compound 11 obtained by the synthetic example 11 (1.0 g, 0.24 mmol) and N-methylglycine (0.20 g, 2.2 mmol) were added to hexafluorotetrachlorobutane (15 mL), and orthodichlorobenzene (30 mL) solution of $C_{60}$ fullerene (0.06 g, 0.08 mmol) was rapidly added to the obtained mixture. A Dimroth condenser was attached, and the mixture was heated by a hot water bath set at 180° C. and refluxed for 5 hours while stirring. After condensing the reaction mixture cooled to room temperature by a rotary evaporator, the reaction mixture was dissolved in an appropriate amount of AK-225 and filtered. The obtained solution was washed by pure water (50 mL) and dried by magnesium sulfate. After filtering and condensing it by a rotary evaporator, a black oily crude product (0.32 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 9 to 12 MPa, extractable impurities those not including a fullerene backbone were removed. Thereafter, the pressure was raised to 28 MPa, and 0.18 g of a black oily material (a chemical compound 13) was extracted.

Synthetic Example 14

[Formula 14]

Synthesis of Chemical Compound 14 (C14):

Orthodichlorobenzene (50 mL) solution of $C_{60}$ fullerene (0.64 g, 0.89 mmol) was rapidly added to a mixture of 4-formyl-1,2,5-benzenetricarboxylic acid trimethyl ester (0.62 g, 2.2 mmol) and N-methylglycine (0.98 g, 11 mmol).

The mixture was heated by a hot water bath set at 150° C., and stirred for 3 hours. After condensing the reaction mixture cooled to room temperature by a rotary evaporator, the reaction mixture was dissolved in an appropriate amount of toluene and filtered. The obtained solution was condensed by a rotary evaporator to obtain a black solid crude product (2.4 g). By purified by silica gel column chromatography (developing solvent: toluene-ethyl acetate (9:1)), a fullerene derivative including three pyrrolidine rings (a chemical compound 14) was obtained as a black solid (0.34 g, 0.21 mmol, yield 23%).

Synthetic Example 15

[Formula 15]

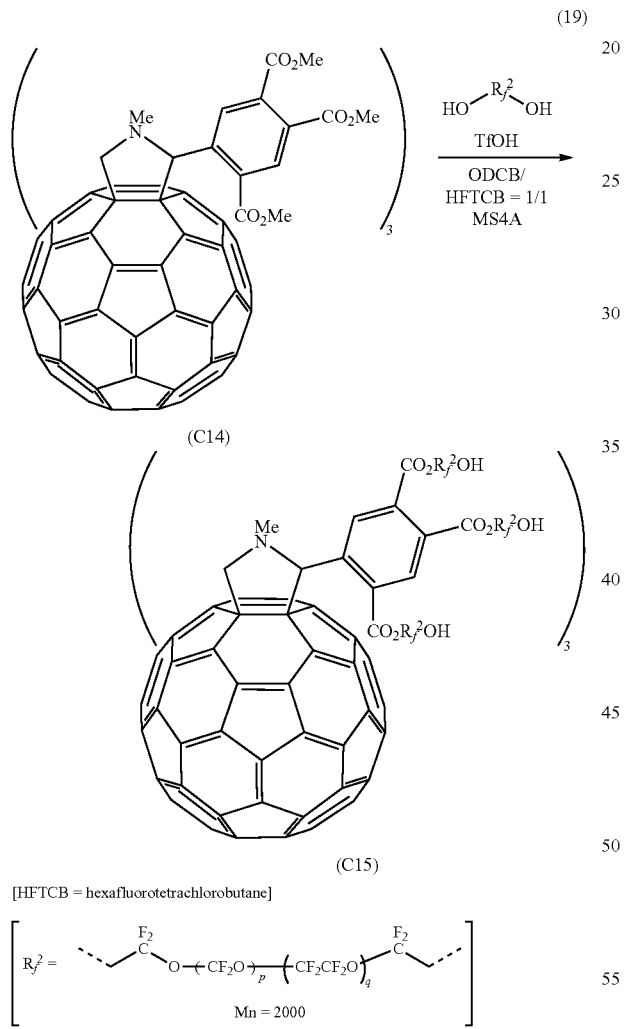

Synthesis of Chemical Compound 15 (C15):

Hexafluoro tetrachlorobutane (60 mL) solution of FOMBLIN ZDOL (manufactured by Solvay Specialty Polymers, 3.8 g, 1.9 mmol) whose number average molecular weight (Mn) was approximately 2000 was added to orthodichlorobenzene (60 mL) solution of the chemical compound 14 obtained by the synthetic example 14 (0.19 g, 0.11 mmol). After dropping trifluoromethanesulfonic acid (1 mL) to the obtained mixture, a Soxhlet extractor in which molecular sieves 4A were provided and a Dimroth condenser were attached, and the mixture was heated by a hot water bath set at 190° C. and refluxed for 5 hours while stirring. After neutralizing the reaction mixture cooled to room temperature by adding ammonia water (10 mL), the mixture was evaporated by a rotary evaporator. After dissolving the obtained oily material in an appropriate amount of AK-225, by filtering and condensing it by a rotary evaporator, a black oily crude product (3.3 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 10 to 18 MPa, impurities such as unreacted FOMBLIN ZDOL were removed. Thereafter, the pressure was raised to 27 MPa, and 0.17 g of a black oily material (a chemical compound 15) was extracted.

Synthetic Example 16

[Formula 16]

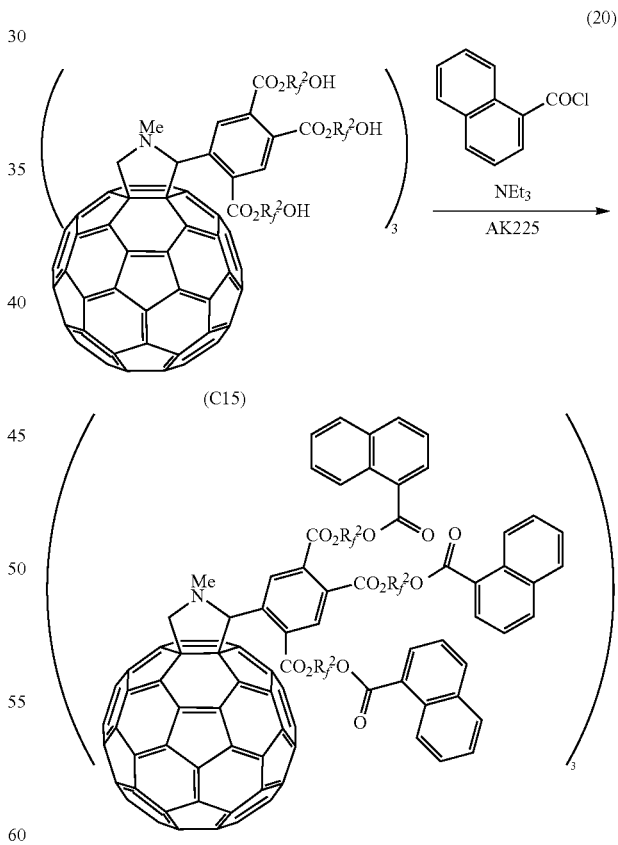

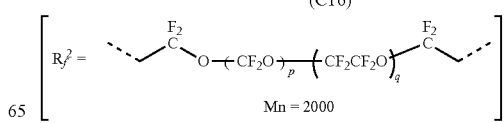

Synthesis of Chemical Compound 16 (C16):

The chemical compound 15 obtained by the synthetic example 15 (0.17 g, 8.7 µmol) and triethylamine (16 mg, 0.16 mmol) were added to AK-225 (10 mL). After cooling the obtained mixture by an ice bath, 1-naphthoyl chloride (20 mg, 0.10 mmol) was added. After returning the mixture to room temperature, the mixture was stirred for 15 hours. After adding ammonia water (1 mL) to the reaction mixture, the mixture was condensed by a rotary evaporator. After dissolving the obtained oily material including white powders in an appropriate amount of tetradecafluorohexane, filtering and condensing it by a rotary evaporator, a black oily crude product (0.10 g) was obtained.

Next, the crude product was introduced in a thickness stainless container having an inlet and an outlet (inner diameter 20 mm×depth 200 mm), and while retaining temperature in the container at 60° C., supercritical carbon dioxide was fed into the container using a supercritical carbon dioxide liquid feeding pump (PU2086-CO2, manufactured by JASCO Corporation) at a liquefied carbon dioxide reduced flow rate of 5 mL/min. By varying the pressure in the container within a range of 10 to 16 MPa, extractable impurities those not including a fullerene backbone were removed. Thereafter, the pressure was raised to 27 MPa, and 73 mg of a black oily material (a chemical compound 16) was extracted. This material was confirmed as the above described chemical compound by the following analysis result of NMR.

$^1$H-NMR δ (ppm): 2.74 (brs, 9H), 4.31 (brs, 36H), 7.47 (brd, 9H), 7.55 (brd, 9H), 7.64 (brd, 9H), 7.90 (brd, 9H), 8.08 (brd, 9H), 8.25 (brd, 9H), 8.94 (brd, 9H).

Example 1

The chemical compound 3 was mixed in tetradecafluorohexane (PF-5060, manufactured by 3M), as the fluorine series solvent, such that the concentration became 0.005 mass %, and whether the compound was dissolved was evaluated by viewing. The result is illustrated in Table 1.

Examples 2 to 7

Solubility was evaluated similarly as example 1 except that each of the chemical compound 5, the chemical compound 7, the chemical compound 8, the chemical compound 12, the chemical compound 13 and the chemical compound 16 was used instead of the chemical compound 3. The results are similarly illustrated in Table 1.

Comparative Example 1

Solubility was evaluated similarly as example 1 except that the following fullerene derivative (a chemical compound 17 (C17)) described in Patent Document 5 (Japanese Patent No. 5600202) was used instead of the chemical compound 3. A result is similarly illustrated in Table 1.

[Chem. 6]

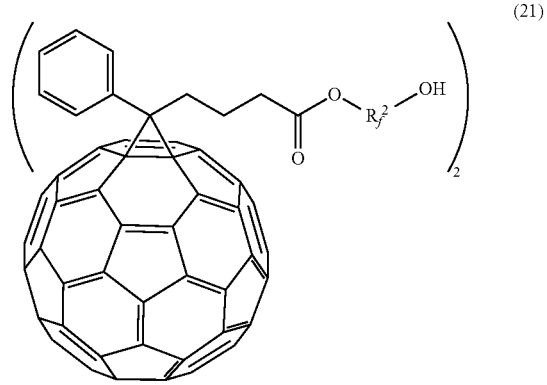

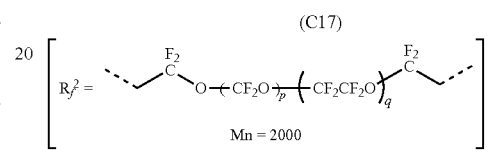

TABLE 1

| | CHEMICAL COMPOUND | TEST RESULT OF SOLUBILITY TO TETRADECAFLUOROHEXANE |
|---|---|---|
| EXAMPLE 1 | C3 | DISSOLVED |
| EXAMPLE 2 | C5 | DISSOLVED |
| EXAMPLE 3 | C7 | DISSOLVED |
| EXAMPLE 4 | C8 | DISSOLVED |
| EXAMPLE 5 | C12 | DISSOLVED |
| EXAMPLE 6 | C13 | DISSOLVED |
| EXAMPLE 7 | C16 | DISSOLVED |
| COMPARATIVE EXAMPLE 1 | C17 | NOT DISOOLVED |

From the above results, it can be understood that the fullerene derivative of the invention has good solubility to tetradecafluorohexane.

Example 8

A simulation disk was manufactured by depositing a carbon protection film made of Diamond-Like Carbon (DLC) on a 2.5-inch glass plank for a magnetic disk by high frequency magnetron sputtering in which carbon was used as a target in Ar gas atmosphere.

Next, as the lubricant, the chemical compound 7 was dissolved in tetradecafluorohexane, and lubricant solutions of concentrations of Table 2, respectively, were prepared.

Next, the lubricant solution was coated on the protection film of the simulation disk by dipping according to the following method. Specifically, the simulation disk was immersed in the lubricant solution provided in a dipping bath of a dip coat apparatus, and the simulation disk was drawn up from the dipping bath to coat the lubricant solution on a surface of the protection film of the simulation disk. Thereafter, by drying the surface on which the lubricant solution was coated, a lubricant layer was formed. The thickness of each of the lubricant layers obtained as such is illustrated in Table 2.

TABLE 2

| CONCENTRATION OF LUBRICANT SOLUTION (MASS %) | THICKNESS (Å) |
| --- | --- |
| 0.001 | 10.4 |
| 0.003 | 10.6 |
| 0.005 | 11.7 |
| 0.01 | 13.8 |

Example 9

The chemical compound 8 was evaluated similarly as example 8. The thickness of each of the lubricant layers is illustrated in Table 3.

TABLE 3

| CONCENTRATION OF LUBRICANT SOLUTION (MASS %) | THICKNESS (Å) |
| --- | --- |
| 0.001 | 7.8 |
| 0.003 | 8.5 |
| 0.005 | 10.4 |
| 0.01 | 11.1 |

Example 10

The chemical compound 12 was evaluated similarly as example 8. The thickness of each of the lubricant layers is illustrated in Table 4.

TABLE 4

| CONCENTRATION OF LUBRICANT SOLUTION (MASS %) | THICKNESS (Å) |
| --- | --- |
| 0.0003 | 5.6 |
| 0.0006 | 7.8 |
| 0.001 | 11.8 |
| 0.015 | 14.4 |

From the above results, the lubricant of the invention has good solubility to tetradecafluorohexane, and a lubricant layer of a hard disk can be formed by using tetradecafluorohexane solution of the lubricant of the invention.

Example 11

Smoothness evaluation of the disk manufactured in example 9 (chemical compound 8, lubricant solution concentration 0.005 mass %) against repeated friction was conducted. When observing a surface of the disk by an optical microscope after performing a load/unload operation by using a SAF tester manufactured by Kubota Corporation, no disorder of smoothness of a disk surface was observed.

Comparative Example 2

Although it was tried to form a lubricant layer similarly as example 9 except that the chemical compound 17 described in Patent Document 5 (Japanese Patent No. 5600202) was used as the lubricant instead of the chemical compound 8, the chemical compound 17 was not dissolved in tetradecafluorohexane, and a lubricant layer could not be formed.

Comparative Example 3

A lubricant layer was formed similarly as example 9 except that the chemical compound 17 described in Patent Document 5 (Japanese Patent No. 5600202) was used as the lubricant instead of the chemical compound 8 and 1,1,1,2,3,4,4,5,5,5-decafluoropentane (manufactured by Du Pont-Mitsui Fluorochemicals Co., Ltd., Vertrel (registered trademark) XF) was used as solvent. The thickness of the lubricant layer obtained as such was 10.5 Å. Further, similarly as example 11, smoothness evaluation against repeated friction was conducted. As a result, irregularity was observed on a circle on which a head was loaded.

By the comparison between example 11 and comparative example 3, it was confirmed that the lubricant of the invention was able to keep smoothness of the lubricated layer surface compared with the lubricant described in Patent Document 5 or the like.

Example 12

A surface of the disk manufactured by a similar method as example 9 was observed using an optical surface analyzer. As a result, it was confirmed that a lubricant coat film was sufficiently uniformly formed. FIG. 1 illustrates an obtained image of distribution of the coat film. Although there are portions in the coat film which seem to be non-uniform at three points at a disk periphery, as they are trails of disk support portions, these were not evaluated as distribution of the coat film.

Example 13

Figure 2:
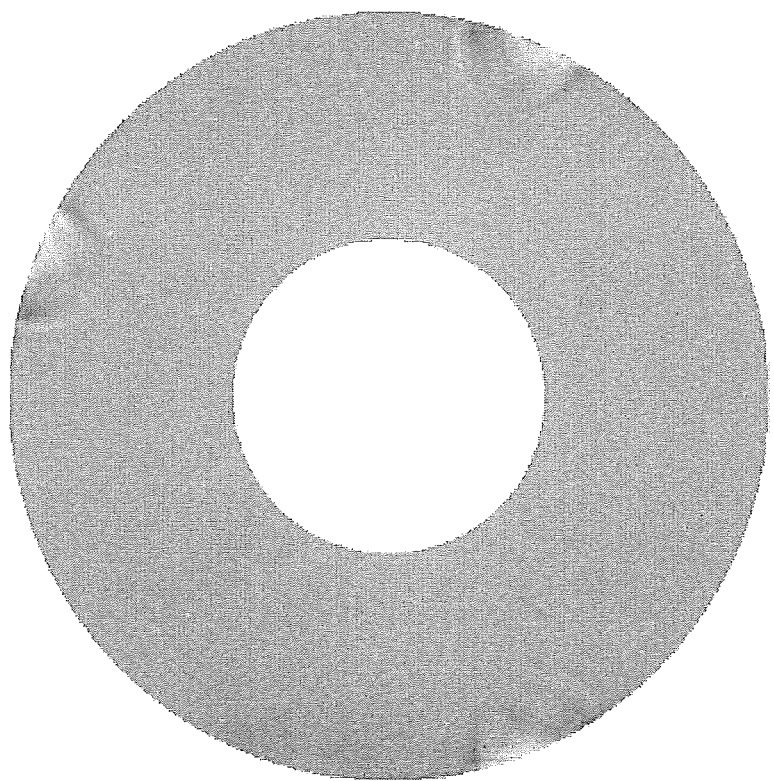
FIG. 2 is a view illustrating a coat film distribution of another example.

A surface of the disk manufactured by a similar method as example 9 except that the chemical compound 12 was used instead of the chemical compound 8 was observed using an optical surface analyzer. As a result, the lubricant coat film was formed more uniform than that of example 12, and linear unevenness of the coat film was not observed on the disk at all. FIG. 2 illustrates an obtained image of distribution of the coat film.

Although the conventional chemical compound (chemical compound 17) has low solubility (Table 1) and could not be coated, when the chemical compound of the invention is used, a sufficiently uniform lubricant coat film can be obtained.

INDUSTRIAL APPLICABILITY

The fullerene derivative of the invention may be preferably used for a lubricant, in particular, for a lubricant for a magnetic recording medium.

What is claimed is:
1. A fullerene derivative comprising, in a molecule:
a fullerene backbone; and
n pyrrolidine rings each being condensed to the fullerene backbone,
each of the pyrrolidine rings including one aryl group including m substituents each including a perfluoropolyether chain, "m" being an integer from 2 to 5 and "n" being an integer from 1 to 5.
2. The fullerene derivative according to claim 1, wherein the fullerene derivative is a chemical compound expressed by the following general formula (1) in which "FLN" is the fullerene backbone, $(A)_m$ indicates the m substituents each including a perfluoropolyether chain, and "$R^1$" is a hydrogen atom or a hydrocarbon group whose carbon number is less than or equal to 24

[Chem. 1]

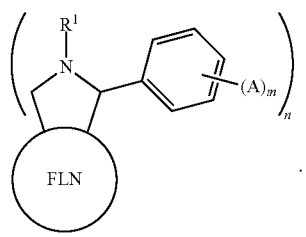

(1)

3. The fullerene derivative according to claim 2, wherein the "$R^1$" is an alkyl group or an aryl group whose carbon number is less than or equal to 24.

4. The fullerene derivative according to claim 1, wherein the fullerene backbone is $C_{60}$.

5. The fullerene derivative according to claim 1, wherein each of the m substituents includes at least a partial structure selected from —$(CF_2)_x$O— in which "x" is an integer from 1 to 5.

6. The fullerene derivative according to claim 5, wherein each of the m substituents includes a partial structure expressed by —$(CF_2CF_2O)_y(CF_2O)_z$— in which each of "y" and "z" is an integer from 1 to 50.

7. The fullerene derivative according to claim 1, wherein each of the m substituents is configured only by a perfluoropolyether structure.

8. The fullerene derivative according to claim 1, wherein each of the m substituents is a straight-chain.

9. A lubricant comprising the fullerene derivative according to claim 1.

10. The lubricant according to claim 9, further comprising a perfluoropolyether chemical compound that does not include a fullerene backbone.

\* \* \* \* \*